(12) United States Patent
Chang et al.

(10) Patent No.: US 6,577,705 B1
(45) Date of Patent: Jun. 10, 2003

(54) COMBINATORIAL MATERIAL ANALYSIS USING X-RAY CAPILLARY OPTICS

(76) Inventors: William Chang, 8592 Peachtree Ave., Newark, CA (US) 94560; Xiao-Dong Xiang, 215 Kevington Pl., Alameda, CA (US) 94502; Edward D. Franco, 216 Avila Rd., San Mateo, CA (US) 94402

( * ) Notice: Subject to any disclaimer, the term of this patent is extended or adjusted under 35 U.S.C. 154(b) by 0 days.

(21) Appl. No.: 09/824,268

(22) Filed: Apr. 2, 2001

(51) Int. Cl.[7] ................................. G01N 23/223
(52) U.S. Cl. ..................... 378/45; 378/71; 378/83
(58) Field of Search .................. 378/44–50, 70–83

(56) References Cited

U.S. PATENT DOCUMENTS 5,612,987 A * 3/1997 Sudo et al. .................. 378/82

* cited by examiner

*Primary Examiner*—Craig E. Church
(74) *Attorney, Agent, or Firm*—John F. Schipper

(57) ABSTRACT

Method and system for analyzing local composition and structure of a compound having one or more non-zero gradients in concentration for one or more selected constituents in a selected direction. A beam of X rays having representative energy E is received by a mono-capillary or poly-capillary device and is directed at a selected small region of the compound. A portion of the X rays is diffracted at the selected region by one or more constituents of the compound, at each of two or more diffraction angles relative to a selected surface or lattice plane(s) of the compound; and the diffracted portion of X rays for each of these diffraction angles is received and analyzed at an X-ray detector. A portion of the X rays excites fluorescence radiation that is received by a fluorescence detector to estimate the relative concentrations in a compound having two or more constituents. Fluorescence X rays and diffraction X rays can be detected at each desired translational position and rotation for a target site. As a result, a concentration map for various constituents in the compound can be prepared, together with a phase map illustrating the structure of a combinatorial compound. An X-ray detector monochromator can be removed and a capillary diameter can be reduced in some situations.

45 Claims, 5 Drawing Sheets

COMBINATORIAL MATERIAL ANALYSIS USING X-RAY CAPILLARY OPTICS

FIELD OF THE INVENTION

This invention relates to X ray characterization of materials using diffraction and fluorescence analysis.

BACKGROUND OF THE INVENTION

Although material synthesis has become more sophisticated in order to produce combinatorially synthesized compounds, analysis of such materials has not kept pace. A combinatorially synthesized material will often have a continuous gradient, rather than a sequence of discontinuous plateaus, in the relative concentration of one or more substances, and use of a broad-brush analysis of local concentration fraction(s) will not suffice to characterize the material. This is especially true for characterization of thin films, where standard transmission and/or reflection analyses may be inadequate to characterize changing concentrations on a small scale.

What is needed is an approach that allows characterization of thin films and similar structures where the relative concentration of one or more material constituents may follow a gradient or other similar pattern. Preferably, the approach should be flexible enough to characterize relative concentrations, gradients and structures on a size scale as low as fractions of a micron.

SUMMARY OF THE INVENTION

These needs are met by the invention, which uses capillary optics combined with X-ray diffraction analysis and X-ray fluorescence analysis to characterize and analyze thin films and similar material structures that may have relative concentration gradients. A capillary optic produces an X-ray beam spot on a target site of a combinatorial material, and diffraction and fluorescence signals are obtained simultaneously at a selected beam energy. For a given beam energy, the location and angular orientation of the target site are varied in a selected manner to obtain the concentration index of one or more constituents of the material, as a function of target site location, and of the diffraction peak position, height and width. The performance can be improved by removal of an energy E monochromator for the X-ray detector and, simultaneously, reduction of a representative diameter of the capillary.

DESCRIPTION OF BEST MODES OF THE INVENTION

Figure 1:
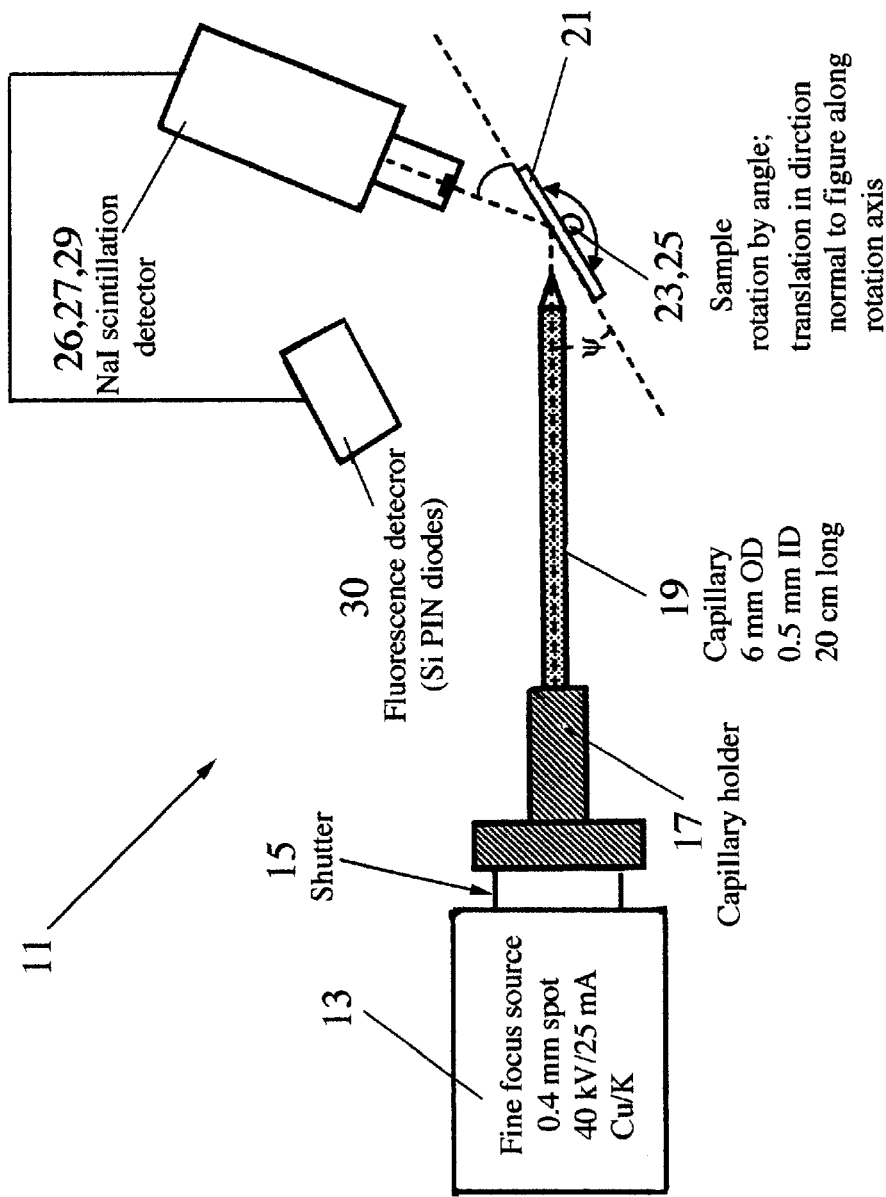
FIG. 1 schematically illustrates apparatus for practicing the invention.

FIG. 1 illustrates apparatus 11 for practicing the invention according to one embodiment, using capillary optics and X-ray diffraction to characterize and analyze a thin film material "in the small." A fine focus X-ray source 13, having high spatial resolution and including a suitable anode material (e.g., Cu, Mo, Fe, Cr, W), whose transmission is controlled by an optional X-ray shutter 15, provides a beam of X rays. Optionally, the shutter 15 provides X-ray exposures over a range of exposure intervals. In a preferred mode of operation, the X-ray, source operates in CW mode and the shutter 15 is not required. X rays transmitted by the shutter 15 are received by a capillary holder 17 and capillary device 19 that transports the X-rays to a small target site on a thin material to be analyzed. The capillary device 19 may, for example, have a straight glass tube with an inner diameter (ID) of 10 $\mu$m–1 mm, a 6 mm outer diameter (OD), an entrance ID of 10 $\mu$m–1 mm, a representative ID at the exit end of about 1–356 $\mu$m, and may have a length of 2–40 cm, or longer, if desired. This much of the apparatus 11 is preferably stationary.

A sample 21 of a selected compound ("target") is positioned to receive X rays delivered by the capillary device 19 at a selected incidence angle $\psi=90°-\theta$($\theta$=diffraction angle) relative to the local surface of the target. The diffraction angle $\theta$(dif) is varied in a selected range, such as 10°–87.5°, depending upon the Bragg angle of diffraction at the target 21, by a rotational stage mechanism 23. A two-theta goniometer, with a 2$\theta$-range of 5°$\leq$2$\theta$$\leq$160° and an accuracy of 0.005°, is suitable for required angular scanning. In FIG. 1, the magnitude of the diffraction angle $\theta$ is exaggerated. A representative X-ray beam focal spot size is in a range of 1–1000 $\mu$m at the sample 21.

If the target 21 has a non-zero (normalized) concentration gradient (e.g., $\Delta\chi=\partial\chi/\partial x$ where $\chi$ is concentration and x is distance measured in a selected direction) for at least one selected constituent of the compound in a first selected direction (e.g., perpendicular to the plane of the paper in FIG. 1), the target is optionally translated by selected amounts $\Delta x_i$ (i=1, 2, . . . ) in a selected range in the first selected direction by a translational stage mechanism 25; and diffraction intensity measurements are performed for at least two distinct values of the variable x, measured in the first direction. If the target 21 has a non-zero concentration gradient $\Delta\chi$ for at least one selected constituent (the same constituent or a second constituent) of the compound in a second selected direction that is transverse to the first direction, the target is optionally translated by selected amounts $\Delta y_i$ (i=1, 2, . . . ) in a selected range in the second selected direction by a translational stage mechanism 25; and diffraction intensity measurements are performed for at least two distinct values of the variable y in the second direction. An error, $\Delta x$(err) or $\Delta y$(err), in translation distance in the first or second direction is usually no more than about 0.1 $\mu$m.

Diffraction intensity measurements are thus performed for translations of the target site in a first direction and in a second transverse direction (not necessarily perpendicular to the first direction), in order to map out the variation in one or more parameters in the first and second directions. This flexibility is useful where the compound has been fabricated using combinatorial synthesis techniques that provide a non-zero concentration gradient for at least one constituent in the compound. Suitable parameters include: concentration of the constituent; separation distance between adjacent planes of the constituent; different lattice parameters for different concentration ranges; and different crystal structures (e.g., face-centered, body-centered) adopted by the compound for different concentration ranges.

X rays diffracted by atomic lattice planes within the target are passed through an energy monochromator 26 and are received by an X-ray collector 27, such as a NaI scintillation detector. The X-ray collector 27 has an associated microprocessor 29 that receives, stores, analyzes and displays alphanumeric and/or graphical; representations of the X-ray data.

Figure 2A:
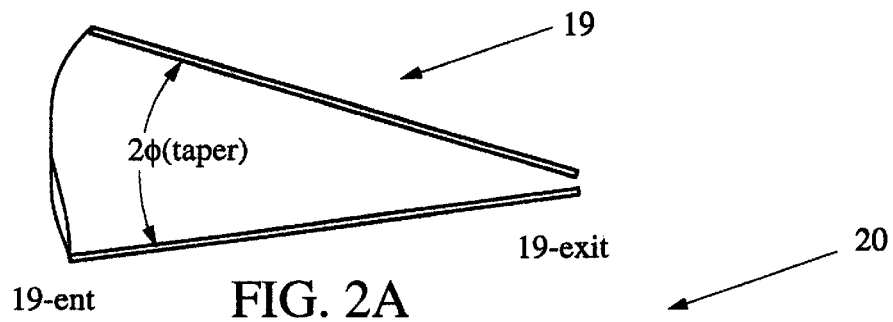
FIGS. 2A and 2B are side views of capillary devices.

A mono-capillary device 19 having an entrance end 19-ent and an exit end 19-exit, illustrated in FIG. 2A, and discussed by E. Hecht, *Optics,* Addison Wesley, Reading Mass., Third Edition 1998, pp. 202–203, and by D. H. Bilderback and E. D. Franco, "Single Capillaries", in *Handbook Of Optics,* Second Edition, Vol. 3, ed. by Michael Bass et al, McGraw-Hill, New York, 2000, pp. 29-1 through 29-7, relies upon total external reflection of a light ray propagating within material having a high refractive index n1 (e.g., glass) and incident upon an interface with a material having a lower refractive index n2 (e.g., air or vacuum), when the angle of incidence $\psi(inc)$ satisfies $$\sin \psi(inc) \geq n2/n1 = \sin \psi(crit). \quad (1)$$

For X rays, this minimum critical angle $\psi(crit)$ is close to 90° (i.e., within 10 mrad, and more preferably within about 4 mrad of 90°). For example, for a glass-vacuum interface with n1=1.52 and n2=1.0, the minimum critical angle for a 10 KeV X ray is $\psi(crit)$=89.8°, and this angle increases toward 90° as the X-ray energy increases. For X-ray energies in a range 5–20 KeV, the minimum critical angle $\psi(crit)$ usually lies in a range 89°–89.95°.

Figure 2B:
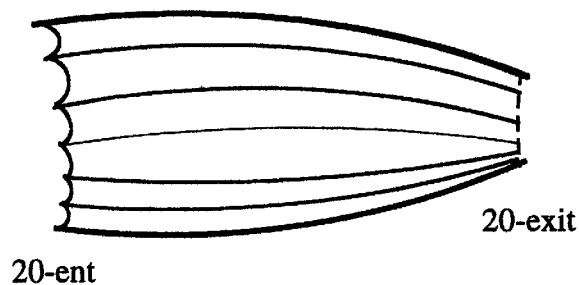

Suitable glasses for capillaries include borosilicates, soda lime glasses, lead-based glasses and silica glasses. Use of glass doped with lead or another suitable, dopant can increase the refractive index n1 at X-ray energies and, thus, can decrease the minimum critical angle $\psi(crit)$, although absorption of X rays within the glass may increase. Using a metal coating on the capillaries, a lower minimum critical angle $\psi(crit)$ and a corresponding increase in efficiency are obtained. Preferably, the distance from the capillary exit end 19-exit to the sample 21 is no more than about 10 mm, in order to preserve beam integrity. Optionally, the capillary device 19 is shielded to prevent radiation leakage beyond its walls.

Where illumination of a site area greater than about 50 $\mu$m is required, the mono-capillary device 19 can be replaced by a poly-capillary device 20, shown in FIG. 2B and available, for example, from X-ray Optical Systems, Inc. of Albany, N.Y. (www.xrayoptics.com). A poly-capillary device typically includes 25–100 individual capillaries, each with a diameter of 5–50 $\mu$m and aligned to accept X rays over a relatively large solid angle, to provide a quasi-parallel or focused X-ray beam at the exit end 20-exit. An advantage of use of a poly-capillary device is that the intensity of an X-ray beam, delivered to a target site with a diameter greater than about 50 $\mu$m, is increased vis-a-vis the intensity of a mono-capillary device, possibly with reduced control on the divergence angle of the incident X-ray beam. A typical X-ray spot size for a poly-capillary is 50–250 $\mu$m.

In a preferred embodiment, the capillary device 19 has a small taper $\phi(taper)$, of the order of 1–5 mrad or has a straight edge. The penetration depth of a grazing incidence X-ray into glass is usually less than 10 nm for many hollow tube capillaries. The capillary device 19 may be configured with tapered capillaries, as demonstrated by E. A. Stern et al, "Simple method for focusing x-rays using tapered capillaries", Appl. Opt., vol. 27 (1988) 5135–5139, and by S. A. Hoffman et al, "Applications of single tapered glass capillaries: submicrometer x-ray imaging and Laue diffraction", Optical Engrg., vol. 33 (1993) 303–306. A taper angle $\phi$ of the order of 1–5 mrad (0.0573°–0.2865°) can be used here, as well as larger or smaller capillary taper angles. By decreasing the taper diameter as one proceeds away from the capillary entrance end 19-ent, the tapered capillary is caused to act as an X-ray funnel, with a correspondingly high X-ray intensity gain factor.

A capillary often manifests broad wavelength band pass. Because the effective refractive index of the capillary material decreases approximately monotonically with increasing X-ray energy, any capillary will have a cut-off X-ray energy, beyond which the reflecting efficiency drops rapidly to zero. Absorption in air increases as the energy decreases toward the lower end of the scale. These two effects provide a broad energy band pass region that may include energies from 0.5 KeV to, about 80 KeV, or higher in some situations.

Figure 3A:
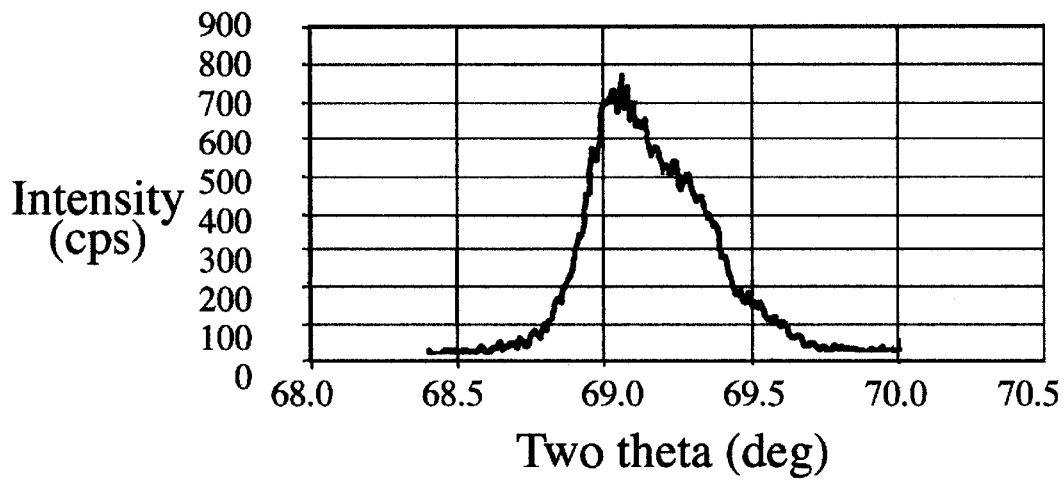
FIGS. 3A and 3B are graphical views of intensity versus diffraction angle for Si, with a 350 $\mu$m and a 50 $\mu$m X-ray beam, respectively.

In order to adequately characterize a combinatorially synthesized compound, the rotational stage mechanism 23 for the apparatus 11 in FIG. 1 preferably provides angular increments $\Delta\theta$ for the diffraction angle of the order of 0.01–0.2° and the translational stage mechanism 25 preferably provides translation increments $\Delta x$ of the order of 1 $\mu$m or larger. FIG. 3A graphically presents variation of diffracted X-ray intensity (expressed in counts per sec), measured as a function of diffraction angle $\theta$, for a semiconductor wafer (here, Si), using Cu/K-shell X rays produced by an X-ray tube with a copper anode operated at 30 kV, and using a 350 $\mu$m diameter capillary, with angular increments $\Delta\theta$=0.02°. For the Si wafer, a local peak X-ray diffraction intensity occurs at $2\theta$=69.1°, but the K$\alpha$1 and K$\alpha$2 lines of Cu are not resolved.

The sample may be primarily a semiconductor material that contains one or more of Si, Ge, Al, Ga, As, In, Sb and other similar atomic species. An example is the compound $Ga_xIn_{1-x}As_ySb_{1-y}$, with the index x varying linearly in a direction of a first coordinate and the index y varying linearly in a direction of a second coordinate. The relative concentration indices may vary linearly or nonlinearly with a location coordinate. Another example is a metal oxide $M1_zM2_{1-z}O_3$, where the index z varies in a selected direction and M1 and M2 are valence-2 and valence-3 metals drawn from a group that includes Ti, Zr, Hf, V, Nb, Ta, Cr, Mo, W, Mn, Tc, Re, Fe, Ru, Os, Co, Rh, Ir, Ni, Pd, Pt, Cu, Ag, Au, Zn, Cd, Hg, B, Al, Ga, In and Tl.

Figure 4:
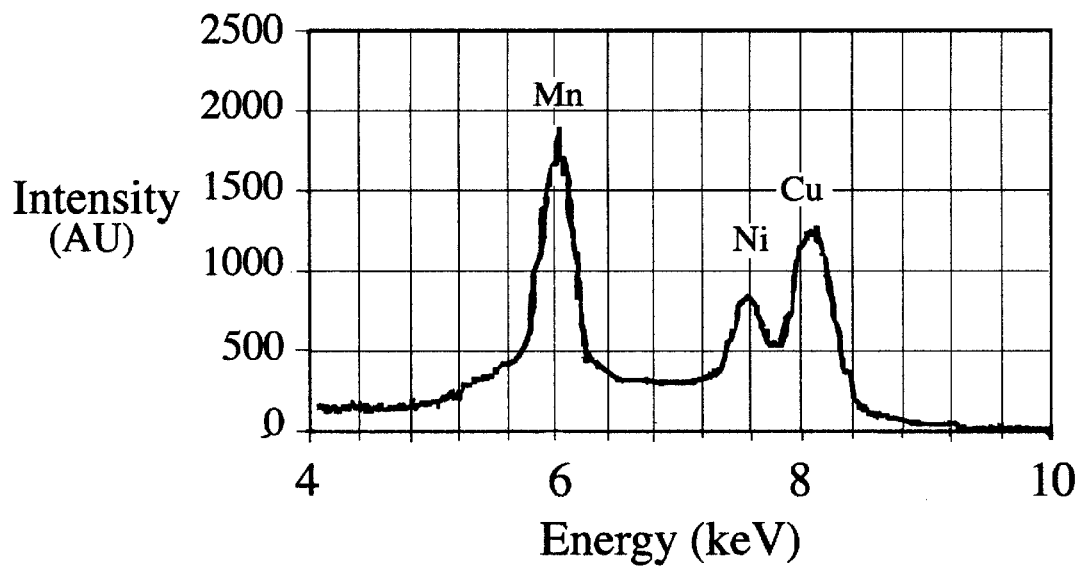
Figure 5:
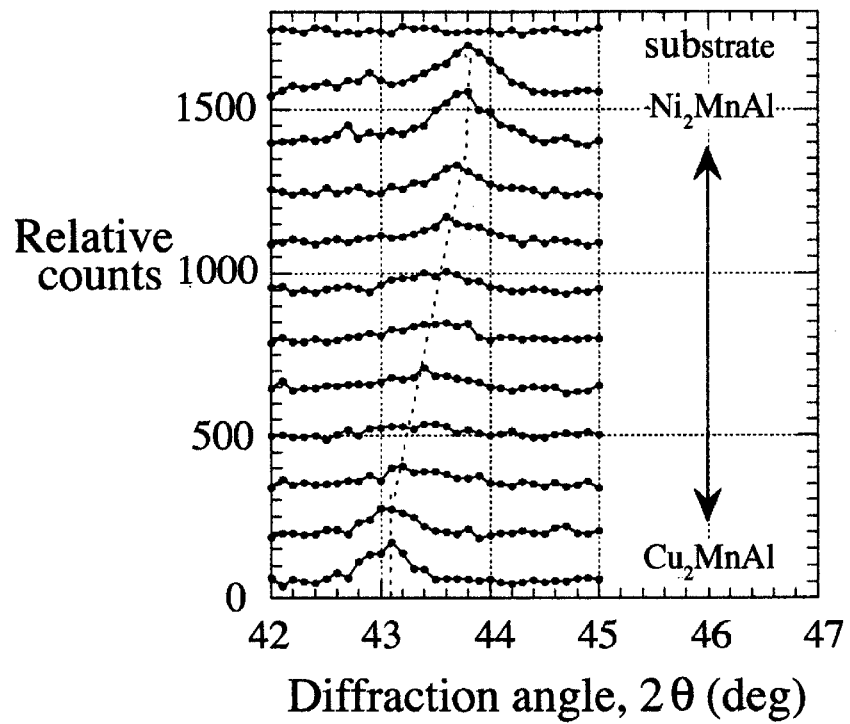

The apparatus 11 includes an X-ray fluorescence detector 30 (e.g., Si PIN diodes), positioned adjacent to the sample 21, to detect and analyze X-ray fluorescence radiation emitted by the sample when irradiated by an X-ray microbeam. This detector may be an Si(Li), an Si PIN or a Ge energy dispersive detector, for example. These detectors and others are described in G. F. Knoll, *Radiation Detection and Measurement,* John Wiley & Sons, New York, 1979. This detection produces a sequence of peaks, each representing fluorescence X rays emitted by a particular element that is present. This is illustrated in FIG. 4 for a combinatorial material $(Ni_2)_zCu_{1-z}MnAl$ for a particular value of a concentration index z. The concentration gradient $\Delta\chi$ is related to the derivative $\partial z/\partial x$ (or $\partial z/\partial y$). In FIG. 4, the Mn, Ni and Cu constituents have fluorescence peaks at energies of about 5.9 KeV, 7.5 KeV and 8.1 KeV, respectively. The Al fluorescence peak (at about 1.5 KeV) is much smaller and requires special measurements (in a vacuum) to obtain its contribution. Because Mn and Al occur in a ratio of 1:1 in this material, it is usually sufficient to measure the Mn fluorescence as representative of the concentration of Mn and of Al present. FIG. 5 graphically illustrates variation of diffraction peak angle $2\theta$ (in a range of 43°–44°) with relative concentrations of Cu and Ni in the combinatorial material $(Ni_2)_zCu_{1-z}MnAl$ ($0 \leq z \leq 1$).

Figure 6:
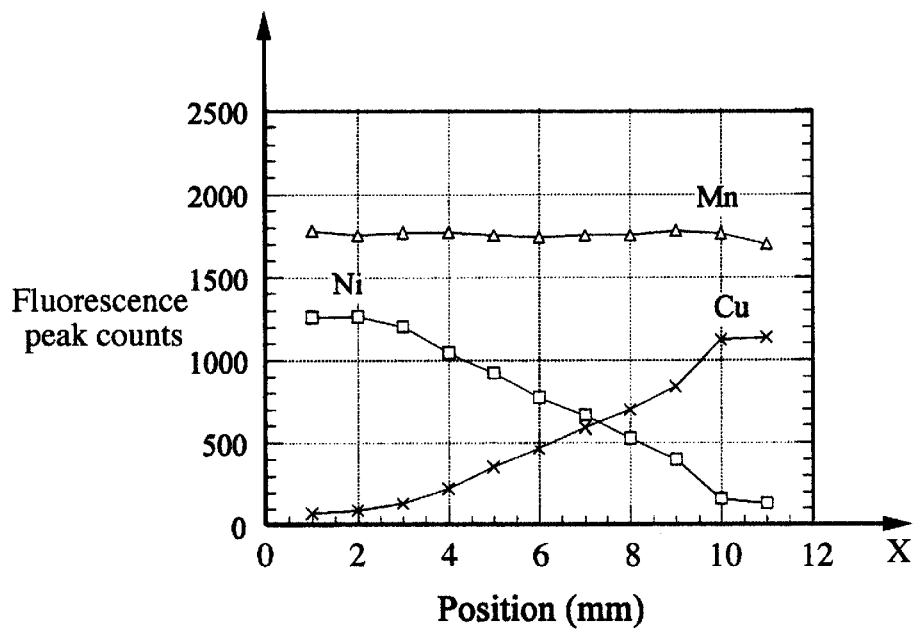
FIGS. 4, 5 and 6 graphically illustrate X-ray fluorescence measurements for three constituents, at fixed values of (x,y,$\theta$(dif)), for varying values of x and X-ray diffraction patterns for varying values of x, for a representative combinatorial material.

As the location coordinate x (or y) is varied by moving the translation stage 25, the concentration will vary, and the relative heights of the Ni and Cu (and possibly Mn) fluorescence peaks, shown in FIG. 4, and the diffraction peak angular position, shown in FIG. 5, will vary correspondingly. FIG. 6 graphically illustrates variation of these fluorescence peak values as the location coordinate x (or y) is varied for the combinatorial material $(Ni_2)_z Cu_{1-z} MnAl$. Note that the Ni peak and the Cu peak are monotonically decreasing and monotonically increasing, respectively, as x varies, indicating that the concentration gradient is of one sign (e.g., negative) for Ni and is of the opposite sign (e.g., positive) for Cu.

The X-ray source 13 in FIG. 1 may operate in a pulse mode or (preferably) in a CW mode. The translation stage (s), 23 and 25, may move in a slew mode with continuous motion or may move in increments, $\Delta x$ and/or $\Delta y$.

From the measurement values illustrated in FIGS. 4, 5 and 6, one can estimate the concentration gradient $\Delta\chi(x)$ for this material for various values of the location coordinate x. For example, if a fluorescence peak for Cu is found to vary (strictly monotonically) as $p = p(\Delta\chi(x))$, the curve for Cu peak values in FIG. 5 can be expressed as $P(x) = p(\Delta\chi(x))$ and can be inverted to provide an estimate, $$\Delta\chi(x) = p^{-1}\{P(x)\}, \quad (2)$$

for the concentration gradient $\Delta\chi(x)$ as a function of the location coordinate x.

Figure 3B:
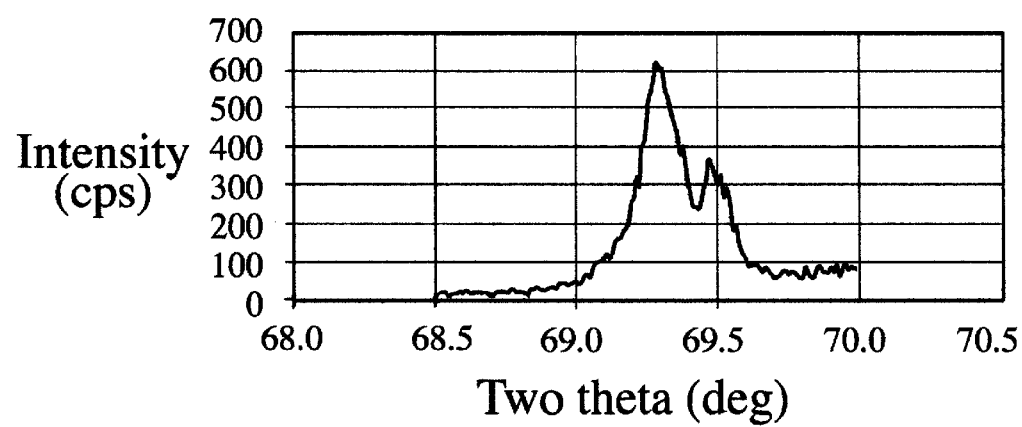

A key insight here is that an X-ray beam is emitted from a capillary device within a narrow cone, with a typical cone angle of 1–5 mrad. The small divergence of this beam is a significant contributor to the overall angular resolution achieved by the instrument. This small beam divergence allows removal of the energy monochromator 26 (FIG. 1) and a corresponding increase in signal intensity. With the energy monochromator removed, the time required to perform a diffraction measurement is significantly reduced by the gain in intensity at the irradiated site. FIG. 3B graphically illustrates variation in X-ray intensity with changing diffraction angle $2\theta$, for the same situation as is illustrated in FIG. 3A, (1) with the energy monochromator removed and (2) using a capillary with a diameter d(cap) reduced from 350 $\mu$m to 50 $\mu$m. The diffraction plot in FIG. 3B shows a double peak (not visible in the plot in FIG. 3A), corresponding to reflection of the Cu $K\alpha 1$ and Cu $K\alpha 2$ X-ray lines. For the combined actions (1) and (2), the net intensity loss is a factor of about 6, the net improvement in angular resolution is a factor of about 2, and the net improvement in spatial resolution is a factor of about 7 ($\approx 350/50$).

These results are unexpected, because removal of the energy monochromator would normally provide a collection of X rays that are less finely resolved. One possible explanation here is that reduction of the capillary; diameter d(cap) compensates for this reduction in energy resolution by providing an X-ray beam that is geometrically smaller. However, this improvement does not rely upon this, or any other, explanation.

Figure 7:
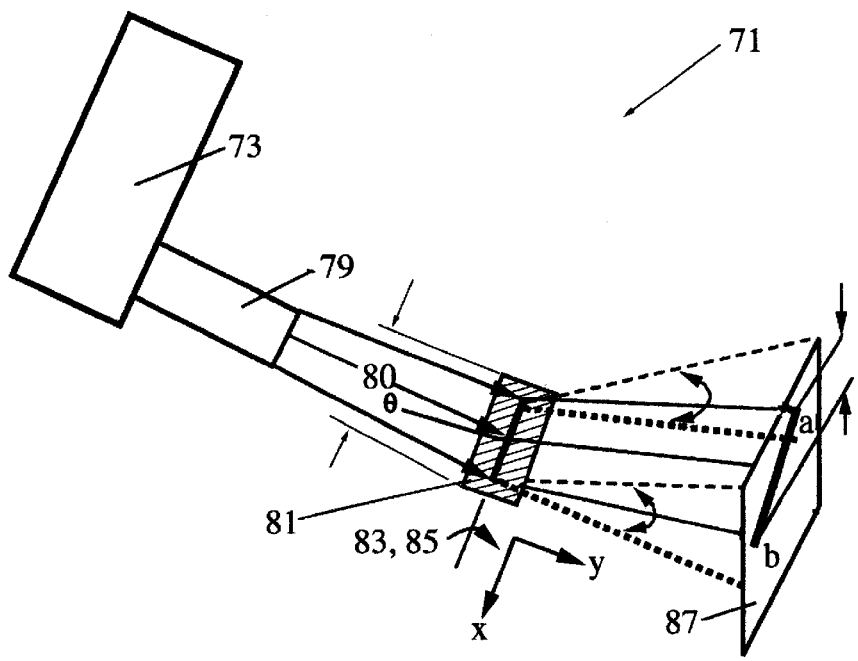
FIGS. 7 and 8 illustrate an alternative configurations for the invention.

In some situations, the capillary device diameter d(cap) may be reduced to a range of 1–50 $\mu$m, without removing the energy monochromator 26 in FIG. 1, in order to retain high energy resolving power. This action might be taken where the concentration gradient $\Delta\chi$ is very high and the sample-to-sample translation distance, $\Delta x$ and/or $\Delta y$, is much smaller (e.g., 5–20 $\mu$m) because of the large change in concentration that occurs over a translation distance such as 50–100 $\mu$m. In this instance, the exposure time may be increased, where a mono-capillary device is used. Where a poly-capillary device is used, as discussed in the preceding, the corresponding exposure time may still be held to reasonable values, of the order of tens of seconds to tens of minutes.

Where only X-ray diffraction information is important, an alternative configuration 71, shown in FIG. 7 for parallel detection of diffraction, may be used. An X-ray source 73 is coupled with a rectangular cross section capillary optic 79 so that a relatively long, thin line 80 of X rays extends across a sample 81 in the direction (x) of a concentration gradient. Preferably, the X rays illuminate a region 80 on the sample that is approximately rectangular or ovular in shape and that has a selected length to width ratio (aspect ratio) that is appropriate for the sample. The diffraction angle $\theta$ is varied by rotating a sample rotation stage 83. A two-dimensional X-ray imaging detector 87 receives and records a diffracted X-ray beam from the sample 81. In the x-direction of the concentration gradient, the inherent diffraction peak angle shifts, corresponding to lattice parameter variation caused by the changing concentration, and this shift is recorded in parallel as an image trace without requiring a linear scan in the x-direction.

Where the sample also has a concentration gradient in a transverse (y) direction, the sample 81 is translated in the y-direction by a sample translation stage 85, and a diffraction image is recorded along a "line" 80 extending in the x-direction for each selected y-coordinate value. Proceeding in this manner, rotation and one-direction scanning (in the y-direction) provides a two-dimensional map of the changing concentration for the sample 81.

Figure 8:
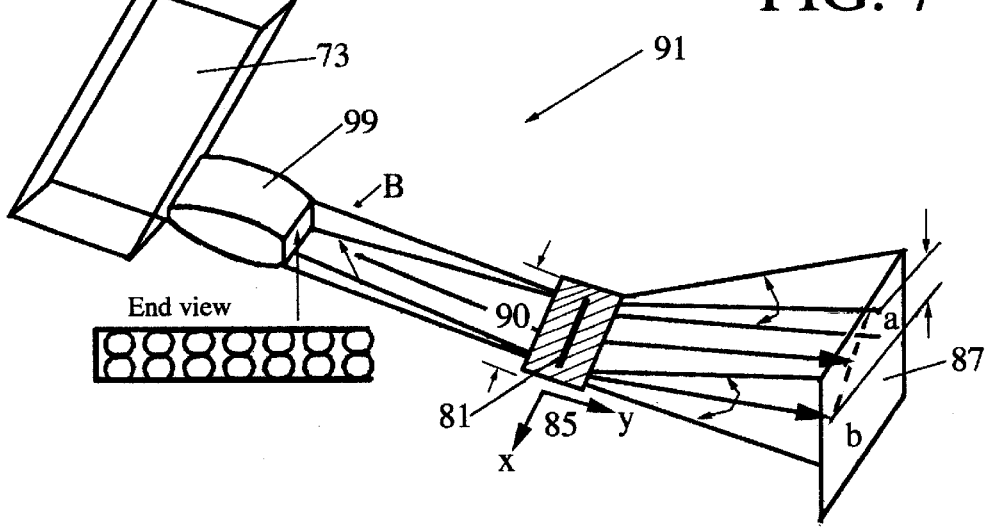

If the angular range of diffraction peaks is relatively small (ten degrees or less), the angular scan provided by a rotating stage 83 with a rectangular capillary optic in FIG. 7 can be replaced by a poly-capillary optic 99 that produces a line 90 of X rays having a large beam divergence angle $\beta$, as illustrated in FIG. 8. In this manner, a parallel detection configuration can be extended to (i) linear X-ray detection in a selected x-direction for a non-zero concentration gradient and (ii) angular X-ray detection over a selected range of diffraction angles, without translation of the sample in the x-direction and without rotation of the sample about an axis corresponding to a changing diffraction angle. Unlike the rectangular capillary 79 in FIG. 7, the poly-capillary 99 in FIG. 8 includes many differently oriented capillaries so that the diffraction peak trace may appear to be spotty and not smoothly varying.

What is claimed is:

1. A method for analyzing local composition of a compound having at least one gradient in concentration of a constituent, the method comprising:

directing a beam of X rays, having energies approximately equal to a representative energy E, through a poly-capillary mechanism to provide an X-ray beam having a convergence angle up to about 100 at a selected compound, located in a selected region, having two or more constituents, and having at least one non-zero gradient in concentration in a selected direction for at least one selected constituent of the compound;

allowing at least a first portion of the X rays to be diffracted at the selected region by the at least one selected constituent of the compound, for each of at least two diffraction angles relative to a selected surface of the compound and to be received and analyzed at an X-ray detection-mechanism, without rotating and without translating the at least one selected compound, without rotating and without translating the poly-capillary mechanism, and without rotating and without translating the X-ray detection mechanism;

allowing a second portion of the X rays to induce fluorescence radiation by the at least one selected constituent; and receiving and analyzing at least a portion of the fluorescence radiation emitted by the at least one selected constituent at a fluorescence detector.

2. The method of claim 1, further comprising allowing said portion of said X rays to be diffracted by said compound at said at least two diffraction angles by orienting said selected surface so that said X rays are incident upon said selected surface of said compound at each of at least two incidence angles.

3. The method of claim 1, further comprising providing said capillary optical mechanism as a tapered capillary mechanism.

4. The method of claim 1 further comprising choosing said representative energy E to lie in a range $0.5 \text{ KeV} \leq E \leq 80 \text{ KeV}$.

5. The method of claim 1, further comprising:

directing X rays, having energies approximately equal to a representative energy E2, along said capillary mechanism to said selected region;

allowing the X rays with representative energy E2 to induce fluorescence radiation by said at least one selected constituent of said compound; and receiving and analyzing at least a portion of fluorescence radiation at the representative energy E2 emitted by said at least one selected constituent at said fluorescence detector.

6. The method of claim 5, further comprising:

analyzing said fluorescence radiation at said first and second representative energies; and estimating a relative concentration of said at least one selected constituent relative to at least one other constituent of said compound.

7. The method of claim 5, further comprising:

allowing at least a fourth portion of said X rays to be diffracted at said selected surface by said at least one selected constituent, for each of at least third and fourth diffraction angles relative to said selected surface of said compound; and receiving and analyzing at least one of said diffracted X-rays of the fourth portion at the at least third and fourth diffraction angles at said X ray detection mechanism.

8. The method of claim 1, further comprising providing at least one of Si, Ge, Ga, In, As, Sb, Mn, Al, Ni and Cu as said at least one selected constituent of said compound.

9. The method of claim 1, further comprising providing said capillary mechanism with a diameter no greater than about 350 µm.

10. The method of claim 1, further comprising providing said capillary mechanism with a selected shape and a selected orientation so that said beam of X rays illuminates said selected region in a pattern that is substantially rectangular or ovular, that is oriented in said selected direction, and that has a selected aspect ratio.

11. The method of claim 10, further comprising:

choosing said selected direction to correspond to a direction of non-zero concentration gradient for said at least one constituent in said compound; and rotating at least one of said selected compound and said capillary mechanism about an axis having an axial direction that is transverse to said selected direction by at least one selected non-zero rotation angle so that said X rays& are diffracted at a second selected region by said at least one selected constituent of said compound.

12. The method of claim 10, further comprising providing said capillary mechanism with a beam divergence angle at least equal to a selected angle.

13. A system for analyzing local composition of a compound having at least one gradient in concentration of a constituent, the system comprising:

a poly-capillary optical mechanism positioned to receive and direct a beam of X rays, having energies approximately equal to a representative energy E, along the poly-capillary mechanism to provide an X-ray beam having a convergence angle up to about 10° at a selected compound, received in a sample holder, located in a selected region, having two or more constituents and having at least one non-zero gradient in concentration in a selected direction for at least one selected constituent of the compound;

an X-ray detection mechanism, positioned to receive and analyze a first portion of the X rays that is diffracted at the selected region by the at least one selected constituent of the compound, for each of at least two diffraction angles relative to a selected surface of the compound, without rotating and without translating the at least one selected compound, without rotating and without translating the poly-capillary mechanism, and without rotating and without translating the detection mechanismt; and a fluorescence detector positioned to receive and analyze at least a portion of fluorescence radiation emitted by the at least one selected constituent.

14. The system of claim 13, wherein said X-ray detection mechanism is positioned relative to said sample holder to receive said portion of said X rays to be diffracted by said compound at said at least two diffraction angles by orienting said selected regions so that said X rays are incident upon said selected region of said compound at each of at least two incidence angles.

15. The system of claim 13, wherein said capillary optical mechanism is a tapered capillary mechanism.

16. The system of claim 13, wherein:

said capillary mechanism receives and directs said X rays, having energies approximately equal to a second representative energy E2, along said capillary mechanism to said selected region;

a third portion of said X rays with representative energy E2 is allowed to induce fluorescence radiation by said at least one selected constituent of said compound; and said fluorescence detector receives and analyzes at least a portion of fluorescence radiation at the representative energy E2 emitted by said at least one selected constituent at said fluorescence detector.

17. The system of claim 16, wherein said fluorescence detector analyzes said fluorescence radiation at said first and second representative energies and estimates a relative concentration of said at least one selected constituent relative to at least one other constituent of said compound.

18. The system of claim 17, wherein said X-ray detection mechanism is positioned relative to said samplesholder to receive and analyze at least a fourth portion of said X rays to be diffracted at said selected region by said at least one selected constituent, for each of at least third and fourth diffraction angles relative to said selected surface of said compound.

19. The system of claim 13, wherein said capillary mechanism has a diameter no greater than about 350 µm.

20. The system of claim 13, wherein said capillary mechanism is provided with a selected shape and a selected orientation so that said beam of X rays illuminates said selected region in a pattern that is substantially rectangular or ovular, that is oriented in said selected direction, and that has a selected aspect ratio.

21. The system of claim 20, wherein:
said capillary mechanism is positioned so that said selected direction corresponds to a direction of non;-zero concentration gradient for said at least one constituent in said compound; and
said selected compound in said sample holder is rotated about an axis having an axial direction that is transverse to said selected direction by at least one selected non-zero rotation angle so that said X rays are diffracted at a second selected region by said at least one selected constituent of said compound.

22. The system of claim 20, wherein said capillary mechanism is provided with a beam divergence angle at least equal to a selected angle.

23. A method for analyzing local composition of a compound having at least one gradient in concentration of a coristituent, the method comprising:
directing a beam of X rays, having energies approximately equal to a representative energy E, through a mono-capillary mechanism having an approximately rectangular cross-section, to a selected compound, located in a selected region, having two or more constituents, and having at least one non-zero gradient in concentration in a selected direction for at least one selected constituent of the compound;
allowing at least a first portion of the X rays to be diffracted at the selected region by the at least one selected constituent of the compound, for each of at least two diffraction angles relative to a selected surface of the compound and to be received and analyzed at an X-ray detection mechanism, without translating the at least one selected compound, without translating the mono-capillary mechanism, and without translating the X-ray detection mechanism;
allowing a second portion of the X rays to induce fluorescence radiation by the at least one selected constituent; and
receiving and analyzing at least a portion of the fluorescence radiation emitted by the at least one selected constituent at a fluorescence detector.

24. The method of claim 23, further comprising allowing said portion of said X rays to be diffracted by said compound at said at least two diffraction angles by orienting said selected surface so that said X rays are incident upon said selected surface of said compound at each of at least two incidence angles.

25. The method of claim 23, further comprising providing said capillary optical mechanism as a tapered capillary mechanism.

26. The method of claim 23, further comprising choosing said representative energy E to lie in a range 0.5 KeV≦E≦80 KeV.

27. The method of claim 23, further comprising:
directing X rays, having energies approximately equal to a representative energy E2, along said capillary mechanism to said selected region;
allowing the X rays with representative energy E2 to induce fluorescence radiation by said at least one selected constituent of said compound; and
receiving and analyzing at least a portion of fluorescence radiation at the representative energy E2 emitted by said at least one selected constituent at said fluorescence detector.

28. The method of claim 27, further comprising:
analyzing said fluorescence radiation at said first and second representative energies; and
estimating a relative concentration of said at least one selected constituent relative to at least one other constituent of said compound.

29. The method of claim 27, further comprising:
allowing at least a fourth portion of said X rays to be diffracted at said selected surface by said at least one selected constituent, for each of at least third and fourth diffraction angles relative to said selected surface of said compound; and
receiving and analyzing at least one of said diffracted X-rays of the fourth portion at the at least third and fourth diffraction angles at said X ray detection mechanism.

30. The method of claim 23, further comprising providing at least one of Si, Ge, Ga, In, As, Sb, Mn, Al, Ni and Cu as said at least one selected constituent of said compound.

31. The method of claim 23, further comprising providing said capillary mechanism with a diameter no greater than about 350 µm.

32. The method of claim 23, further comprising providing said capillary mechanism with a selected shape and a selected orientation so that said beam of X rays illuminates said selected region in a pattern that is substantially rectangular or ovular, that is oriented in said selected direction, and that has a selected aspect ratio.

33. The method of claim 32, further comprising:
choosing said selected direction to correspond to a direction of non-zero concentration gradient for said at least one constituent in said compound; and
rotating at least one of said selected compound and said capillary mechanism about an axis having an axial direction that is transverse to said selected direction by at least one selected non-zero rotation angle so that said X rays are diffracted at a second selected region by said at least one selected constituent of said compound.

34. The method of claim 32, further comprising providing said capillary mechanism with a beam divergence angle at least equal to a selected angle.

35. The method of claim 34, further comprising receiving and analyzing said diffracted X rays without rotating said selected compound and without rotating said capillary mechanism about an axis having an axial direction that is transverse to said selected direction.

36. A system for analyzing local composition of a compound having at least one gradient in concentration of a constituent, the system comprising:
a mono-capillary optical mechanism, having an approximately rectangular cross-section and positioned to receive and direct a beam of X rays, having energies approximately equal to a representative energy E, along the mono-capillary mechanism to a selected compound, received in a sample holder, located in a selected region, having two or more constituents, and having at least one non-zero gradient in concentration in a selected direction for at least one selected constituent of the compound;
an X-ray detection mechanism, positioned to receive and analyze a first portion of the X rays that is diffracted at the selected region by the at least one selected constituent of the compound, for each of at least two diffraction angles relative to a selected surface of the compound, without translating the at least one selected compound, without translating the mono-capillary mechanism, and without translating the detection mechanism; and a fluorescence detector positioned to receive and analyze at least a portion of fluorescence radiation emitted by the at least one selected constituent.

37. The system of claim 36, wherein said capillary optical mechanism is a tapered capillary mechanism.

38. The system of claim 36, wherein:
said capillary mechanism receives and directs said X rays, having energies approximately equal to a second representative energy E2, along said capillary mechanism to said selected region;

a third portion of said X rays with representative energy E2 is allowed to induce fluorescence radiation by said at least one selected constituent of said compound; and said fluorescence detector receives and analyzes at least a portion of fluorescence radiation at the representative energy E2 emitted by said at least one selected constituent at said fluorescence detector.

39. The system of claim 38, wherein said fluorescence detector analyzes said fluorescence radiation at said first-and second representative energies and estimates a relative concentration of said at least one selected constituent relative to at least one other constituent of said compound.

40. The system of claim 39, wherein said X-ray detection mechanism is positioned relative to said sample holder to receive and analyze at least a fourth portion of said X rays to be diffracted at said selected region by said at least one selected constituent, for each of at least third and fourth diffraction angles relative to said selected surface of said compound.

41. The system of claim 36, wherein said capillary mechanism has a diameter no greater than about 350 $\mu$m.

42. The system of claim 36, wherein said capillary mechanism is provided with a selected shape and a selected orientation so that said beam of X rays illuminates said selected region in a pattern that is substantially rectangular or ovular, that is oriented in said selected direction, and that has a selected aspect ratio.

43. The system of claim 42, wherein:
said capillary mechanism is positioned so that said selected direction corresponds to a direction of non-zero concentration gradient for said at least one constituent in said compound; and said selected compound in said sample holder is rotated about an axis having an axial direction that is transverse to said selected direction by at least one selected non-zero rotation angle so that said X rays are diffracted at a second selected region by said at least one selected constituent of said compound.

44. The system of claim 42, wherein said capillary mechanism is provided with a beam divergence angle at least equal to a selected angle.

45. The system of claim 36, wherein said X-ray detection mechanism is positioned relative to said sample holder to receive said portion of said X rays to be diffracted by said compound at said at least two diffraction angles by orienting said selected region so that said X rays are incident upon said selected region of said compound at each of at least two incidence angles.

* * * * *